United States Patent
Lee et al.

(10) Patent No.: US 12,390,556 B2
(45) Date of Patent: Aug. 19, 2025

(54) NANOCOMPOSITE MATERIALS COMPRISING CATIONIC NANOPARTICLES AND ANIONIC POLYMERS USEFUL IN METHODS FOR 3D PRINTING THEREOF

(71) Applicant: ETH ZÜRICH, Zürich (CH)

(72) Inventors: Mihyun Lee, Zürich (CH); Marcy Zenobi-Wong, Zürich (CH); Jin Chang, Zürich (CH)

(73) Assignee: ETH ZÜRICH, Zürich (CH)

( * ) Notice: Subject to any disclaimer, the term of this patent is extended or adjusted under 35 U.S.C. 154(b) by 1109 days.

(21) Appl. No.: 16/000,679

(22) Filed: Jun. 5, 2018

(65) Prior Publication Data
US 2019/0010288 A1    Jan. 10, 2019

(30) Foreign Application Priority Data
Jun. 27, 2017    (WO) .................. PCT/IB2017/053845

(51) Int. Cl.
*B33Y 30/00*    (2015.01)
*A61L 27/38*    (2006.01)
(Continued)

(52) U.S. Cl.
CPC ....... *A61L 27/3804* (2013.01); *A61L 27/3813* (2013.01); *A61L 27/3817* (2013.01); *A61L 27/3826* (2013.01); *A61L 27/3834* (2013.01); *A61L 27/446* (2013.01); *A61L 27/52* (2013.01); *A61L 27/54* (2013.01); *B33Y 70/00* (2014.12); *C08G 73/02* (2013.01); *C08K 3/02* (2013.01); *C08L 1/02* (2013.01); *C09D 11/03* (2013.01); *C09D 11/38* (2013.01); *A61L 27/18* (2013.01); *A61L 27/26* (2013.01); *A61L 2300/258* (2013.01); *A61L 2300/414* (2013.01);
(Continued)

(58) Field of Classification Search
None
See application file for complete search history.

(56) References Cited

U.S. PATENT DOCUMENTS 8,551,525 B2 * 10/2013 Cook ..................... A61L 27/24
                                                       424/491
9,983,195 B2 *  5/2018 King .................. G01N 33/5011
(Continued)

FOREIGN PATENT DOCUMENTS

| CN | 103285427 | * | 9/2013 |
| WO | 2011035573 | * | 3/2011 |
| WO | 2016138702 | * | 9/2016 |

OTHER PUBLICATIONS

Madhumathi, K. et al. "Novel Chitin/nano-silica composite . . . ". International Journal of Biological Macromolecules. 289-292 (2009). (Year: 2009).*

(Continued)

*Primary Examiner* — Sheng H Davis
(74) *Attorney, Agent, or Firm* — Foley & Lardner LLP

(57) ABSTRACT

The present technology provides nanocomposite compositions that include about 0.1 wt. % to about 40 wt. % of nanoparticles having a net cationic charge by weight of the composition; about 0.1 wt. % to about 50 wt. % of one or more gelling agents by weight of the composition; and a
(Continued)

solvent that includes a protic solvent. Methods of preparing a three-dimensional structure via the nanocomposite composition are also disclosed.

19 Claims, 9 Drawing Sheets

(51) Int. Cl.

| | | |
|---|---|---|
| A61L 27/44 | (2006.01) | |
| A61L 27/52 | (2006.01) | |
| A61L 27/54 | (2006.01) | |
| B33Y 70/00 | (2020.01) | |
| C08G 73/02 | (2006.01) | |
| C08K 3/02 | (2006.01) | |
| C08L 1/02 | (2006.01) | |
| C09D 11/03 | (2014.01) | |
| C09D 11/38 | (2014.01) | |
| A61L 27/18 | (2006.01) | |
| A61L 27/26 | (2006.01) | |
| B05D 5/00 | (2006.01) | |
| B82Y 40/00 | (2011.01) | |
| C08G 83/00 | (2006.01) | |

(52) U.S. Cl.
CPC ... *A61L 2300/426* (2013.01); *A61L 2300/428* (2013.01); *A61L 2400/12* (2013.01); *B05D 5/00* (2013.01); *B33Y 30/00* (2014.12); *B82Y 40/00* (2013.01); *C08G 83/003* (2013.01); *C08K 2003/023* (2013.01); *C08L 2203/02* (2013.01)

(56) References Cited

U.S. PATENT DOCUMENTS

| | | | |
|---|---|---|---|
| 2005/0186337 A1* | 8/2005 | Bringley | B01J 13/0008 |
| | | | 427/220 |
| 2007/0026069 A1* | 2/2007 | Shastri | A61K 9/06 |
| | | | 424/486 |
| 2011/0274742 A1 | 11/2011 | Arinzeh et al. | |
| 2014/0137770 A1* | 5/2014 | Raab | B01J 13/0034 |
| | | | 106/160.1 |
| 2014/0335184 A1 | 11/2014 | Park et al. | |
| 2018/0141996 A1* | 5/2018 | Rickus | C12N 11/14 |
| 2018/0296343 A1* | 10/2018 | Wei | B29C 64/386 |
| 2019/0224914 A1* | 7/2019 | Matzner | B33Y 70/00 |

OTHER PUBLICATIONS

Polylysine Pub. Chem Compound Summary. 20223. (Year: 2023).*
International Preliminary Report on Patentability PCT/IB2017/053845 dated Jan. 9, 2020.
International Search Report and Written Opinion for PCT/IB2017/053845; dated Nov. 17, 2017; 15 pages.
Kai Zhu et al., "Gold Nanocomposite Bioink for Printing 3D Cardiac Constructs", Advanced Functional Materials, vol. 27, No. 12, dated Jan. 17, 2017, 12 pages.
Domingos et al: "Characterizing Manufactured Nanoparticles in the Environment: Multimethod Determination of Particle Sizes" retrieved by McGill University on Oct. 1, 2009, http://pubs.acs.org, Publication date: Apr. 30, 2009.
Examination Report on AU application No. 2018203875 dated Jul. 19, 2023.
Examination Report re Canadian Application No. 3006955 issued on Nov. 30, 2023.

* cited by examiner

NANOCOMPOSITE MATERIALS COMPRISING CATIONIC NANOPARTICLES AND ANIONIC POLYMERS USEFUL IN METHODS FOR 3D PRINTING THEREOF

FOREIGN PRIORITY CLAIM

This application claims the benefit of priority under 35 USC § 119(a) to International Application No. PCT/IB2017/053845, filed Jun. 27, 2017, the entire contents of which are incorporated herein by reference for any and all purposes.

FIELD

The present technology relates generally to nanocomposite compositions and methods suitable for use as printable hydrogel inks. More particularly, and not by way of limitation, the present technology relates to nanocomposite compositions and methods suitable for obtaining biocompatible three-dimensional structures via 3D printing methods.

BACKGROUND

Three-dimensional (3D) printing is an additive manufacturing technique that enables the direct production of three-dimensional constructs. This technique is advantageous in broad applications, including production of 3D architectures of tissues or organs for transplants and implants. While 3D printing technology can facilitate direct generation of 3D engineered tissue, currently available hydrogel systems yield unfavorable properties, e.g., mechanical strength, rheology, and degree of swelling.

The present technology is directed to overcoming these and other deficiencies.

SUMMARY

In an aspect, a nanocomposite composition is provided that includes about 0.1 wt. % to about 40 wt. % of nanoparticles having a net cationic charge by weight of the composition; about 0.1 wt. % to about 50 wt. % of one or more gelling agents by weight of the composition; and a solvent that includes a protic solvent.

In a related aspect, a method of preparing a three-dimensional structure is provided, wherein the method includes using a nanocomposite composition of any embodiment described herein to fabricate the three-dimensional structure. The method may optionally include contacting the three-dimensional structure with a cross-linking agent subsequent to fabricating the three-dimensional structure.

In a further related aspect, a kit for fabricating a nanocomposite composition of any embodiment herein is provided. The kit includes nanoparticles having a net cationic charge; one or more gelling agents; and instructions for generation of the nanocomposite composition, wherein the nanocomposite composition includes about 0.1 wt. % to about 40 wt. % of the nanoparticles by weight of the composition; about 0.1 wt. % to about 50 wt. % of the one or more gelling agents by weight of the composition; and a solvent that includes a protic solvent.

Another related aspect is directed to the three-dimensional structure of the present technology provided by any aspect or embodiment described herein. The three-dimensional structure may be provided by a process that includes using a nanocomposite composition of any embodiment herein to fabricate the three-dimensional structure; and, optionally, contacting the three-dimensional structure with a cross-linking agent subsequent to fabricating of the three-dimensional structure.

BRIEF DESCRIPTION OF THE DRAWINGS

FIG. 7A illustrates use of the nanocomposite composition of the present technology (Ink A), and FIG. 7B illustrates the results from a comparative ink having no nanoparticles having a cationic charge (Ink C).

FIG. 8A provides a printed cube using Ink C at a 20 mm/s extrusion rate. FIG. 8B provides a printed cube using Ink C at a 14 mm/s extrusion rate and ionically cross-linked for 1 h in a 100 mM $CaCl_2$ solution. FIG. 8C provides a printed cube using Ink A at a 20 mm/s extrusion rate and ionically cross-linked for 1 h in a 100 mM $CaCl_2$ solution.

DETAILED DESCRIPTION

Figure 1:
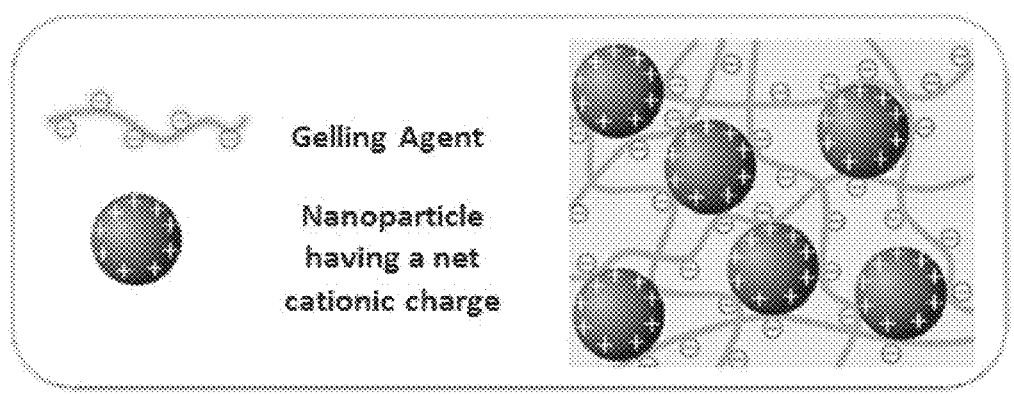
FIG. 1 shows a schematic of the nanocomposite composition of the present technology that includes nanoparticles having a net cationic charge and a gelling agent (anionic polymer).

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

The following terms are used throughout and are as defined below.

As used herein, "about" when used before a numerical designation, e.g., temperature, time, amount, and concentration including range, will mean up to plus or minus 10% of the particular term. Accordingly, unless indicated to the contrary, the numerical parameters set forth in the following specification and attached claims are approximations. Each numerical parameter should at least be construed in light of the number reported significant digits and by applying ordinary rounding techniques.

The use of the terms "a" and "an" and "the" and similar references in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Non-covalent cross-linking of the gelling agents as described herein is well known in the art as illustrated by, but not limited to, the following references: Appel, E. A. et al., *Exploiting Electrostatic Interactions in Polymer-Nanoparticle Hydrogels*, ACS Macro Lett., 2015, 4, 848-852; Appel, E. A. et al., *Self-assembled hydrogels utilizing polymer-nanoparticle interactions*, 2014, Nat. Comm., 2015, 6:6295; Jungst, T. et al., *Strategies and Molecular Design for 3D Printable Hydrogels*, Chem. Rev., 2016, 116, 1496-1539.

The term "shear stress" or "shear-thinning" refers to the rheological viscoelastic properties of a material related to fluid-like or non-fluid-like behavior and flow. Shear stress and shear-thinning include properties related to Bingham flow, plastic flow, pseudoplasticity, dilatancy, thixotropy, rheopexy, and the like or other stress and/or strain properties of a viscous material. Further, "shear-thinning" refers to a reduction in apparent viscosity (the ratio of shear stress to the shear rate) with increasing (pseudoplastic), time dependent (thixotropic) or associated with a yield stress, defined as a stress that must be exceeded before flow starts, (Bingham plastics and generalized Bingham plastics). See generally, Harris, J., & Wilkinson, W. L., "Non-Newtonian Fluid," pp. 856-858 in Parker, S. P., ed., McGraw-Hill Encyclopedia of Physics, Second Edition, McGraw-Hill, New York, 1993.

The preset technology provides nanocomposite compositions and methods for printing three-dimensional structures from the nanocomposite compositions. In certain aspects, the present technology relates to a nanocomposite composition. In another aspect, the present technology relates to methods of printing a three-dimensional structure from the nanocomposite composition.

In an aspect, a nanocomposite composition includes about 0.1 weight percent ("wt. %") to about 40 wt. % of nanoparticles by weight of the composition; about 0.1 wt. % to about 50 wt. % of one or more gelling agents by weight of the composition; and a solvent that includes a protic solvent. The term "nanoparticle" as used herein refers to particles with weight average diameters of less than 1 micrometer (μm) but at least about 1 nanometer (nm). The nanoparticles have a net cationic charge. The net charge may include a plurality of charged functional groups disposed on the surface of the nanoparticle. The nanoparticles may include (a) cationic nanoparticle cores, or (b) non-cationic nanoparticle cores with a cationic coating material disposed on the outer surface of each non-cationic nanoparticle core, or (c) a mixture of (a) and (b).

The compositions of the present technology provide electrostatically cross-linked hydrogels (FIG. 1) having strong but reversible interactions between the nanoparticles and gelling agents. For example, the reversible interaction between nanoparticles having a net cationic charge and gelling agents having a net anionic charge result in the formation of the nanocomposite composition having superior shear-thinning properties, high mechanical strength, and a low degree of swelling. Such properties are advantageous over use of gelling agents alone or in systems lacking the electrostatic interactions in the nanocomposite compositions of the present technology. Additionally, the present nanocomposite compositions do not require the gelling agents to be chemically modified for cross-linking by the nanoparticles. Thus, the nanoparticles of the nanocomposite composition are capable of initiating non-covalent cross-linking of gelling agents to generate the reversible hydrogels suitable for 3D printing of high fidelity three-dimensional structures.

The nanocomposite composition includes the nanoparticles in an amount of about 0.1 wt. % to about 40 wt. % by weight of the composition. Thus, the nanoparticles may be included in an amount of about 0.1 wt. %, about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 12 wt. %, about 15 wt. %, about 18 wt. %, about 20 wt. %, about 25 wt. %, about 30 wt. %, about 35 wt. %, about 40 wt. %, or any range including and/or in between any two of these values. For example, in any embodiment herein, the nanocomposite composition may include about 1 wt. % to about 10 wt. % of the nanoparticles, and may preferably include about 2 wt. % to about 7 wt. % of the nanoparticles.

The nanoparticles may have a weight average diameter of about 1 nm to about 900 nm. Thus, the weight average diameter may be about 1 nm, about 5 nm, about 10 nm, about 15 nm, about 20 nm, about 25 nm, about 30 nm, about 35 nm, about 40 nm, about 45 nm, about 50 nm, about 55 nm, about 60 nm, about 70 nm, about 80 nm, about 90 nm, about 100 nm, about 150 nm, about 200 nm, about 250 nm, about 300 nm, about 400 nm, about 500 nm, about 600 nm, about 700 nm, about 800 nm, about 900 nm, or any range including and/or in between any two of these values. For example, in any embodiment herein the weight average diameter may be about 20 nm to about 300 nm, and may preferably be about 25 nm to about 200 nm.

In any embodiment herein, the nanocomposite composition may include the nanoparticles in an amount of about 2 wt. % to about 7 wt. % by weight of the composition and a weight average diameter of about 25 nm to about 200 nm.

Suitable types of cationic nanoparticle cores for the nanocomposite compositions include, but are not limited to, chitosan nanoparticles, amine-functionalized silica nanoparticles, amine-functionalized polystyrene nanoparticles, cationic polyamidoamine dendrimer (PAMAM) nanoparticles, and combinations of any two or more thereof. Such cationic nanoparticle cores may be uncoated.

In any embodiment herein, the nanoparticles may include a non-cationic nanoparticle core. The non-cationic nanoparticle core may be an anionic nanoparticle core (i.e., the nanoparticle core exhibits a net anionic charge) or a non-ionic nanoparticle core. The cationic coating material disposed on the outer surface of such non-cationic nanoparticle cores provides the nanoparticle with a net cationic charge. Non-ionic nanoparticle cores include polystyrene nanoparticles, poly(D,L-lactide-co-glycolide) nanoparticles, graphene nanoparticles, poly(ethylene glycol) ("PEG")-polylactide nanoparticles, cellulose nanoparticles, magnetic nanoparticles, silver nanoparticles, gold nanoparticles, albumin nanoparticles, silk nanoparticles, gelatin nanoparticles, elastin nanoparticles, or a combination of any two or more thereof. Anionic nanoparticle cores include, but are not limited to, silica nanoparticles, mesoporous silica nanoparticles, biodegradable silica nanoparticles, carboxylate-functionalized polystyrene nanoparticles, and combinations of any two or more thereof. Suitable coating materials may include, but are not limited to, branched poly(ethyleneimine), linear poly(ethyleneimine), poly(allylamine), polylysine (such as poly-L-lysine or poly-D-lysine), polyhistidine (such as poly-L-histidine or poly-D-histidine), polyarginine (such as poly-L-arginine or poly-D-arginine), cetyltrimethylammonium bromide (CTAB), guanidine, or a combination of any two or more thereof. In any embodiment herein, the coating material may be branched poly(ethyleneimine) or linear poly(ethyleneimine). The aforementioned surface modification of the nanoparticle core with the coating material may be performed by processes known in the art, including but not limited to, dopamine-assisted coating methods as described in Kang, S. M. et al., *One-Step Multipurpose Surface Functionalization by Adhesive Catecholamine*, Adv. Funct. Mater., 2012, 22: 2949-2955. Other suitable molecules may be used to assist surface modification of the nanoparticle core, including but not limited to, molecules having an amine, thiol, catechol, or quaternary ammonium moiety.

Notably, the nanoparticles of the nanocomposite composition are capable of initiating cross-linking of one or more gelling agents to generate a reversible hydrogel system. More specifically, the one or more gelling agents are capable of cross-linking without further chemical modification due to the presence of the nanoparticles. Desirable properties of the one or more gelling agents may include materials having biocompatibility, biodegradability, and biological activity. The gelling agents of the present technology include, but are not limited to, synthetic or natural polymers having a net anionic charge. Suitable gelling agents may include, but are not limited to, alginate, alginate sulfate, gellan gum, acylated gellan gum, gellan sulfate, carboxymethylcellulose, carrageen, carrageen sulfate, guar gum, cassia gum, konjac gum, Arabic gum, ghatti gum, locust bean gum, xanthan gum, xanthan gum sulfate, hyaluronic acid, hyaluronan sulfate, dextran, dextran sulfate, chondroitin, chondroitin sulfate, heparin, heparin sulfate, gelatin, collagen, polysiloxanes, fibrin, chitosan, silk, cellulose, elastin, tropoelastin, dermatan sulfate, pectin, and combinations of any two or more thereof.

Gellan gum refers to a water-soluble polysaccharide, originally produced by a bacterium such as *Pseudomonas elodea*. The repeating unit of the polymer is a tetrasaccharide, which consists of two residues of D glucose and one of each residues of L-rhamnose and D-glucuronic acid. The repeat includes the following structure: $[\beta\text{-D-Glc}p(\beta \rightarrow 4)\text{-}\beta\text{-D-Glc}pA(\beta 1 \rightarrow 4)\text{-}\beta\text{-D-Glc}p(1 \rightarrow 4)\text{-}\alpha\text{-L-Rha}p(1 \rightarrow 3)]_n$. As used herein, the term "gellan gum" refers to both non-acylated gellan gum and acylated gellan gum.

"Acylated gellan gum" refers to gellan that includes an acetate in one or more (including all) oxygen 5' positions and glycerate in one or more (including all) oxygen 2' positions of the glucose unit. The acylated gellan gum may have a degree of acylation of about 10% to about 100% of the available acylation groups, such as about 10% to about 90%, about 10% to about 80%, about 10% to about 70%, about 10% to about 60%, about 10% to about 50%, and any range including and/or in between any two of these values. The acylated gellan gum may include a degree of acylation of about 10%, about 15%, about 20%, about 25%, about 30%, about 35%, about 40%, about 45%, about 50%, about 60%, about 70%, about 80%, about 90%, about 100%, or any range including and/or in between any two of these values. While not being bound by theory, the presence of acylated gellan gum may enhance cross-linking to achieve different degrees of stiffness to achieve better flexibility for structures provided by compositions of the present technology.

Alginate refers to polymers that include two monosaccharides, β-D-mannuronic acid (M) and α-L-guluronic acid (G), arranged in homopolymeric (poly-mannuronate or poly-guluronate) or heteropolymeric block structures. Alginate may be extracted from brown seaweed and does not exert any strong immunological reaction when injected into mammalian tissues. See Suzuki et al., J. Biomed. Mater. Res., 1998, 39:317-322. Alginate is biocompatible, FDA-approved, and used widely in tissue engineering, regenerative medicine, cell encapsulation and drug delivery. Its properties can be tuned by varying the amount of α-L-guluronic acid (G) and (1,4)-linked β-D-mannuronic acid (M) and by functionalization with growth factors and adhesion molecules, such as a RGD-peptide (arginylglycylaspartic acid).

The term "polysaccharide" refers to sugars linked via O-glycosidic bonds. Generally, polysaccharides are capable of forming hydrogels, such as through intermolecular electrostatic interactions. Anionic polysaccharide gelling agents as described herein in any embodiment may have a weight average molecular weight in the range from about 1 kDa to about 10,000 kDa. Suitable weight average molecular weights include, but are not limited to, about 1 kDa to about 10,000 kDa, about 10 kDa to about 2,000 kDa, about 100 kDa to about 1,000 kDa, and ranges between any two of these values. The weight average molecular weight of an anionic polysaccharide gelling agent of any embodiment herein thus may be about 1 kDa, about 5 kDa, about 10 kDa, about 50 kDa, about 100 kDa, about 200 kDa, about 500 kDa, about 1,000 kDa, about 2,500 kDa, about 5,000 kDa, about 7,500 kDa, about 10,000 kDa, or any range including and/or in between any two of these values.

The nanocomposite composition may include the one or more gelling agents in an amount from about 0.1 wt. % to about 50 wt. %. Suitable amounts of the one or more gelling agents may include, but are not limited to, about 0.1 wt. % to about 50 wt. %, about 1 wt. % to about 25 wt. %, about 1 wt. % to about 15 wt. %, about 1 wt. % to about 10 wt. %, about 2 wt. % to about 10 wt. %, about 3 wt. % to about 9 wt. %, about 3 wt. % to about 12 wt. %, about 5 wt. % to about 20 wt. %, and ranges between any two of these values. For example, in a preferred embodiment herein, the nanocomposite composition may include about 2 wt. % to about 10 wt. % of the one or more gelling agents. The amount of the one or more gelling agents in the nanocomposite composition may include, but is not limited to, about 0.1 wt. %, about 0.5 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 12 wt. %, about 15 wt. %, about 20 wt. %, about 25 wt. %, about 30 wt. %, about 35 wt. %, about 40 wt. %, about 45 wt. %, about 50 wt. %, and any range including and/or in between any two of these values.

In any embodiment herein, it may be that a weight ratio of the nanoparticles to the one or more gelling agents is about 1:20 to about 20:1. Thus, the weight ratio may be about 1:20, about 1:19, about 1:18, about 1:17, about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, or any range including and/or in between any two of these values. As an illustration, in any embodiment herein, the weight ratio of nanoparticles to the one or more gelling agents may be about 1:1 to about 1:5.

The nanocomposite composition of the present technology includes a protic solvent and optionally an aprotic solvent. Protic solvents as used herein include, but are not limited to, alcohols (e.g., methanol ($CH_3OH$), ethanol (EtOH), isopropanol (iPrOH), trifluoroethanol (TFE), butanol (BuOH), ethylene glycol, propylene glycol), carboxylic acids (e.g., formic acid, acetic acid, propanoic acid, butanoic acid, pentanoic acid, lauric acid, stearic acid, deoxycholic acid, glutamic acid, glucuronic acid), ammonia ($NH_3$), a primary amino compound (e.g., methyl amine, ethyl amine, propyl amine), a secondary amino compound (e.g., dimethyl amine, diethyl amine, di(n-propyl) amine), water, or a mixture of any two or more thereof. Thus, in any of the embodiments and aspects herein, the protic solvent may include an alcohol, a carboxylic acid, a primary amino compound, a secondary amino compound, water, or a mixture of any two or more thereof. In any embodiment herein, the protic solvent may include water, such as deionized water. The amount of protic solvent in the composition may be about 40 wt. %, about 45 wt. %, about 50 wt. %, about 55 wt. %, about 60 wt. %, about 65 wt. %, about 70 wt. %, about 75 wt. %, about 80 wt. %, about 85 wt. %, about 90 wt. %, about 95 wt. %, about 99 wt. %, or any range including and/or in between any two of these values. In particular, the amount of water in the composition may be about 5 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, about 65 wt. %, about 70 wt. %, about 75 wt. %, about 80 wt. %, about 85 wt. %, about 90 wt. %, about 95 wt. %, about 99 wt. %, or any range including and/or in between any two of these values. When the nanocomposite composition includes cells, tissue, growth factors, or a combination of two or more thereof (discussed further herein), the nanocomposite composition preferably excludes protic solvents other than water.

The composition may also include an aprotic solvent. Such aprotic solvents may enhance the rheological properties, stability, and/or usability of the composition as an ink in 3D printing. For example, the aprotic solvent may be selected such that aprotic solvent may be preferentially removed after use of the composition. An aprotic solvent as used herein includes, but is not limited to, a carbonate, a halogenated solvent, an ether, an ester, a ketone, a tertiary amide, a nitrile, a sulfoxide, a sulfone, or a mixture of any two or more thereof. In any of the above embodiments and aspects, the aprotic solvent may be a polar aprotic solvent. Polar aprotic solvents as used herein include, but are not limited to, ethers (e.g., tetrahydrofuran (THF), 2-methyltetrahydrofuran (2Me-THF), dimethoxyethane (DME), dioxane), esters (e.g., ethyl acetate, isopropyl acetate), ketones (e.g., acetone, methylethyl ketone, methyl isobutyl ketone), carbonates (e.g., ethylene carbonate, propylene carbonate, trimethylene carbonate), amides (e.g., dimethylformamide (DMF), dimethylacetamide (DMA)), nitriles (e.g., acetonitrile ($CH_3CN$), propionitrile ($CH_3CH_2CN$), benzonitrile (PhCN)), sulfoxides (e.g., dimethyl sulfoxide), sulfones (e.g., sulfolane), or a mixture of any two or more thereof. In any of the embodiments and aspects herein, the aprotic solvent may include a cyclic carbonate such as ethylene carbonate, propylene carbonate, butylene carbonate, trimethylene carbonate, 2,2-dimethyltrimethylene carbonate, a cyclic ester such as α-acetolactone, β-propiolactone, γ-butyrolactone, γ-valerolactone, δ-valerolactone, γ-caprolactone, δ-caprolactone, ε-caprolactone, or a combination of any two or more thereof. In any of the embodiments and aspects herein, the amount of aprotic solvent in the composition may be about 0.1 wt. %, about 1 wt. %, about 5 wt. %, about 10 wt. %, about 15 wt. %, about 20 wt. %, about 25 wt. %, about 30 wt. %, about 35 wt. %, about 40 wt. %, about 45 wt. %, about 50 wt. %, about 55 wt. %, about 60 wt. %, or any range including and/or in between any two of these values. When the nanocomposite composition includes cells, tissue, growth factors, or a combination of two or more thereof (discussed further herein), the nanocomposite composition preferably excludes aprotic solvents.

While specific solvents have been disclosed, numerous other solvents that would be known to those having ordinary skill in the art having the present disclosure before them are likewise contemplated for use. In any embodiment herein, the solvent may include deionized water.

The nanocomposite composition of the present technology may form a hydrogel system. While not being bound by theory, the non-covalent cross-linking of the nanocomposite composition exploits electrostatic interactions between the nanoparticles (having a net cationic charge) and the anionic charge of the one or more gelling agents. Such electrostatic interactions drive the cross-linking of the gelling agents to obtain the surprisingly superior shear-thinning and self-healing properties of the nanocomposite compositions of the present technology. The nanocomposite composition may optionally undergo additional externally triggered cross-linking in the presence of cross-linking agents, as discussed further herein.

The nanocomposite composition of the present technology may further include cells, tissue, or combinations thereof. Suitable cells include mammalian cells, including but not limited to bovine cells, murine cells, and human cells. Suitable human cells include, but are not limited to, spheroids, pellets, and microtissues. Suitable human cell types include, but are not limited to, primary chondrocytes, primary chondrocytes, chondroprogenitor cells, chondroblasts, mesenchymal stem cells, induced pluripotent stem cells, adipose-derived stem cells, neural crest derived stem cells, fibroblasts, keratinocytes, cardiomyocytes, or combinations of any two or more thereof. The cells described herein in any embodiment may be autologous or allogeneic cells.

Exemplary tissues include, but are not limited to, articular cartilage, nucleus pulposus, meniscus, costal cartilage, trachea, nasal cartilage, rib cartilage, ear cartilage, synovial fluid, tracheal cartilage, vitreous humor, brain, liver, spinal cord, muscle, connective tissues, subcutaneous fat, infrapatellar fat pad, small intestinal submucosa, skin, heart, or a combination of any two or more thereof. In any embodiment herein, the tissue may be cartilage, nucleus pulposus, meniscus, or a combination of any two or more thereof. The tissue may be subject to decellularization to remove epitopes which can cause acute inflammatory responses and pathogens including HIV. Decellularization methods are readily known by one of ordinary skill in the art as illustrated by, but not limited to, Hoshiba et al., *Decellularization Matrices for Tissue Engineering*, Expert Opin. Biol. Ther., 2010; 10:1717-28. For example, decellularization may include the use of detergents, hydrogen peroxide, sodium hydroxide, enzymes, RNase, DNase, or combinations of any two or more thereof.

The nanocomposite composition of the present technology may further include, in any embodiment herein, growth factors. Growth factors include, but are not limited to, BMP-2, BMP-7, TGF-β 1,2,3, FGF-2, IGF-1, or combinations of two or more thereof.

The nanocomposite composition of the present technology may further include, in any embodiment herein, drugs, cytokines, biologics, siRNA, DNA, antioxidants, or combinations of any two or more thereof.

The nanocomposite compositions of the present technology include compositions that comply with Good Manufacturing Practice (GMP) guidelines, as promulgated by the U.S. Food and Drug Administration, for example.

In a related aspect of the present technology, a method is provided for preparing a three-dimensional structure using the nanocomposite composition described herein in any embodiment. The method includes using a nanocomposite composition of any embodiment herein to fabricate a three-dimensional structure. The method optionally includes contacting the three-dimensional structure with a cross-linking agent subsequent to formation of the three-dimensional structure.

Fabricating the three-dimensional structure may include depositing the nanocomposite composition into a three-dimensional structure. The depositing may include the nanocomposite composition to provide part or all of the three-dimensional structure. Such depositing may include one or more of injection molding, rotational molding, positive molds, negative molds, subtractive manufacturing, and 3D printing methods.

Fabricating the three-dimensional structure may include 3D printing. The 3D printing include obtaining the three-dimensional structure on the basis of a three-dimensional computer model. In any embodiment herein, the computer based model may include a three-dimensional model of a contralateral organ of a patient. As used herein, the term "subject" or "patient" is a mammal, such as a cat, dog, rodent or primate. Typically, the subject or patient is human, and preferably in need of transplants or implants for tissue regeneration. The term "subject" and "patient" can be used interchangeably. The computer based three-dimensional model may be obtained via three-dimensional imaging tools. Suitable three-dimensional imaging tools include, but are not limited to, clinical computed tomography (CT), magnetic resonance imaging (MM), laser scanning, 3D cameras, or combinations of any two or more thereof. The 3D printing methods may include additive manufacturing methods. Suitable additive manufacturing methods include ink jet printing, bioprinting, extrusion printing, or layer-by-layer printing. Extrusion printing may include an extrusion rate of about 0.1 mm/s to about 100 mm/s of a nanocomposite composition of any embodiment herein. Suitable extrusion rates include, about 0.1 mm/s to about 10 mm/s, about 0.1 mm/s to about 5 mm/s, about 10 mm/s to about 100 mm/s, about 12 mm/s to about 100 mm/s, about 15 mm/s to about 90 mm/s, about 20 mm/s to about 80 mm/s, about 25 mm/s to about 75 mm/s, about 50 mm/s to about 100 mm/s, or any range including and/or in between any two of these values.

Fabricating the three-dimensional structure may include generation of customized structures of various shapes and sizes for a number of clinical applications. Suitable clinical applications include, but are not limited to, three-dimensional structures for craniofacial applications, orthopaedic applications, skin augmentation, skin grafts, engineered cartilage tissue, or a combination of any two or more thereof. Suitable three-dimensional structures for clinical applications include, but are not limited to, cartilage, avascularized cartilage, heart, skin, auricular grafts, or a combination of any two or more thereof.

The method of the present technology optionally includes contacting the three-dimensional structure with a cross-linking agent subsequent to formation of the three-dimensional structure. Suitable cross-linking agents include, but are not limited to, mono-, di-, or trivalent cations, enzyme, photo initiator, hydrogen peroxide, horseradish peroxidase, or a combination of any two or more thereof. In any embodiment herein, the cross-linking agent may be a monovalent cation, divalent cation, trivalent cation, or combinations of any two or more thereof. Suitable divalent cations include strontium ions, barium ions, calcium ions, or a combination of any two or more thereof.

The cross-linking agents may be part of an aqueous solution that includes one or more of the cross-linking agents. Suitable concentrations of cross-linking agents in the aqueous solution include, but are not limited to, about 10 mM, about 15 mM, about 20 mM, about 25 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 250 mM, about 300 mM, about 350 mM, about 400 mM, or any range including and/or in between any two of these values.

The method may further include incorporating one or more cells, tissue, growth factors, drugs, cytokines, biologics, siRNA, DNA, and antioxidants (discussed previously herein) in the three-dimensional structure. The incorporating may occur before, after, or both before and after, fabricating the three-dimensional structure. In any embodiment herein, the incorporating step may involve the nanocomposite composition including the one or more cells, tissue, growth factors, drugs, cytokines, biologics, siRNA, DNA, and antioxidants prior to fabricating the three-dimensional structure. In any embodiment herein, the incorporating step may involve contacting the three-dimensional structure with the one or more cells, tissue, growth factors, drugs, cytokines, biologics, siRNA, DNA, and antioxidants.

In a further related aspect, a kit for fabricating a nanocomposite composition of any embodiment herein is provided. Thus, the kit includes nanoparticles having a net cationic charge, one or more gelling agents; and instructions for generation of the nanocomposite composition, wherein the nanocomposite composition includes about 0.1 wt. % to about 40 wt. % of the nanoparticles by weight of the composition; about 0.1 wt. % to about 50 wt. % of the one or more gelling agents by weight of the composition; and a solvent that includes a protic solvent. The nanoparticles may include (a) cationic nanoparticle cores, or (b) non-cationic nanoparticle cores with a cationic coating material disposed on the outer surface of each non-cationic nanoparticle core, or (c) a mixture of (a) and (b).

Another related aspect is directed to a three-dimensional structure of the present technology provided by any aspect or embodiment described herein. The three-dimensional structure may be provided by a process that includes using a nanocomposite composition in any embodiment herein to fabricate the three-dimensional; and optionally, contacting the three-dimensional structure with a cross-linking agent subsequent to the fabricating the three-dimensional structure. The three-dimensional structure may include cells and or tissues (discussed herein). The three-dimensional structure may include growth factors (discussed herein). The three-dimensional structure may include one or more of drugs, cytokines, biologics, siRNA, DNA, and antioxidants (discussed previously herein). Preparation of the three-dimensional structure may include contacting the three-dimensional structure with cells subsequent to fabricating the three-dimensional structure. In any embodiment herein, the three-dimensional structure may be in the form of an organ, such as a contralateral organ. The fabricating step may include one or more of ink jet printing, bioprinting, extrusion printing, and layer-by-layer printing. The cross-linking agent, when used, may include a monovalent cation, a divalent cation, a trivalent cation, an enzyme, hydrogen peroxide, horseradish peroxidase, photo initiator, or a combination of any two or more thereof.

The present technology, thus generally described, will be understood more readily by reference to the following examples, which are provided by way of illustration and are not intended to be limiting of the present technology.

EXAMPLES

Example 1: Preparation of Poly(Ethyleneimine) Coated Silica Nanoparticles

Figure 2:
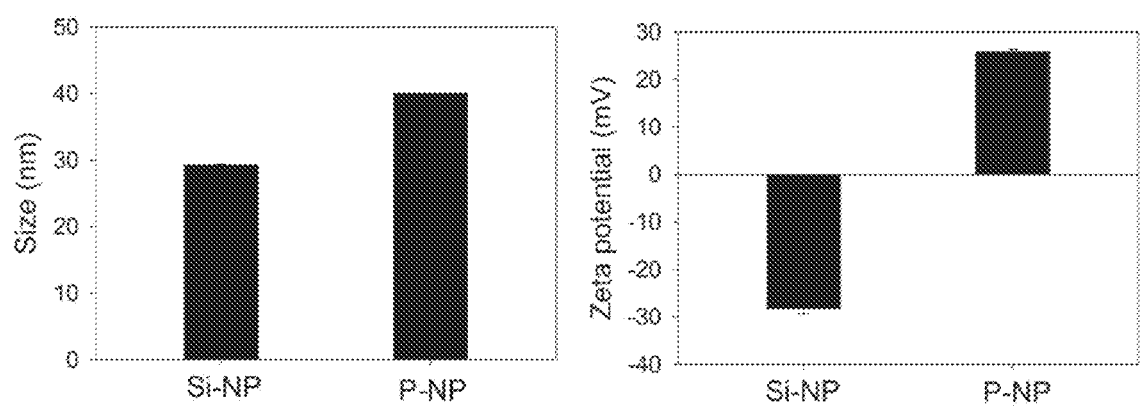
FIG. 2 is a graphical illustration of the sizes and surface zeta potentials of uncoated silica nanoparticles (Si-NP) and poly(ethyleneimine) coated silica nanoparticles (P-NP).

A 3.6 mL solution of 4 wt. % branched poly(ethyleneimine) (2 kDa) was added to 3.6 mL of a 50 wt. % silica nanoparticle aqueous dispersion (ca. 25 nm weight average diameter). The solutions were maintained at a pH of 3, and followed by addition of a 0.4 mL of a 40 mg/mL aqueous solution of dopamine and 0.4 mL of a 72 mg/mL aqueous solution of sodium periodate to the total mixture. The resultant solution was incubated for 3 h, and uncoated nanoparticles and excess reagents were removed via dialysis (50 kDa molecular weight cutoff) against 0.1 M NaCl and deionized water for three days. Excess reagents were discarded to obtain poly(ethyleneimine) coated silica nanoparticle (P-NP). An net positive charge and increased particle size was observed for the P-NP, whereas the uncoated silica nanoparticles (Si-NP) had a net negative charge and smaller particle size (FIG. 2).

Example 2: Preparation of Nanocomposite Ink with (PEI)-Coated Silica Nanoparticles A nanocomposite ink (Ink A) was prepared according to the embodiments described herein. A 15 mL aqueous dispersion of the (PEI)-coated nanoparticles as prepared in Example 1 were combined with D-glucose, alginate, and a mixture of high-acyl gellan gum (KELCOGEL® CG-HA from CP Kelco ApS) and non-acyl gellan gum (KELCOGEL® CG-LA from CP Kelco ApS, termed a "low acyl gellan gum") to provide final concentrations of 300 mM, 3 wt. %, 2.975 wt. %, and 0.525 wt. % respectively. The high-acyl gellan gum on average includes one glycerate per repeat unit and one acetate per two repeat units. The mixture was heated to 90° C. for 1 h and then stirred at room temperature to obtain the nanocomposite ink. Following the same preparation as described above, nanocomposite inks with uncoated silica nanoparticles (Ink B) and no nanoparticles (Ink C) were also prepared.

Figure 3:
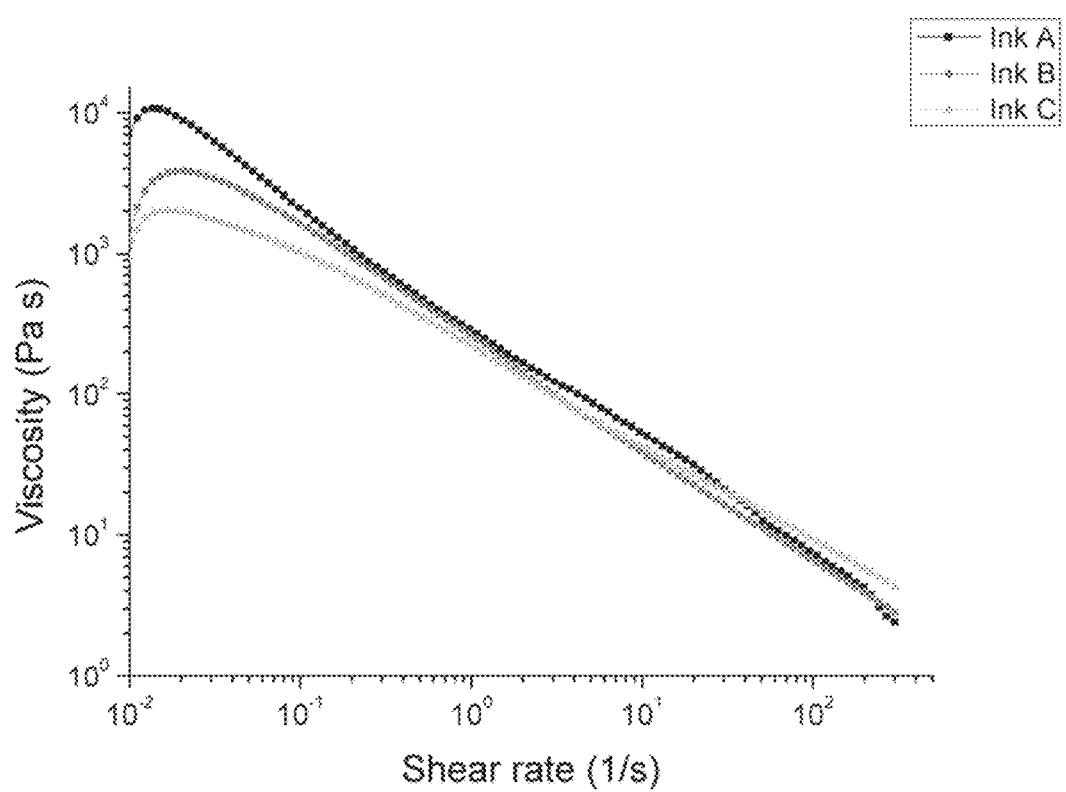
FIG. 3 is a graphical illustration of the shear-thinning behavior of the nanocomposite composition of the present technology (Ink A) and comparative ink compositions (Ink B—uncoated silica nanoparticles; Ink C—no nanoparticles).
Figure 4:
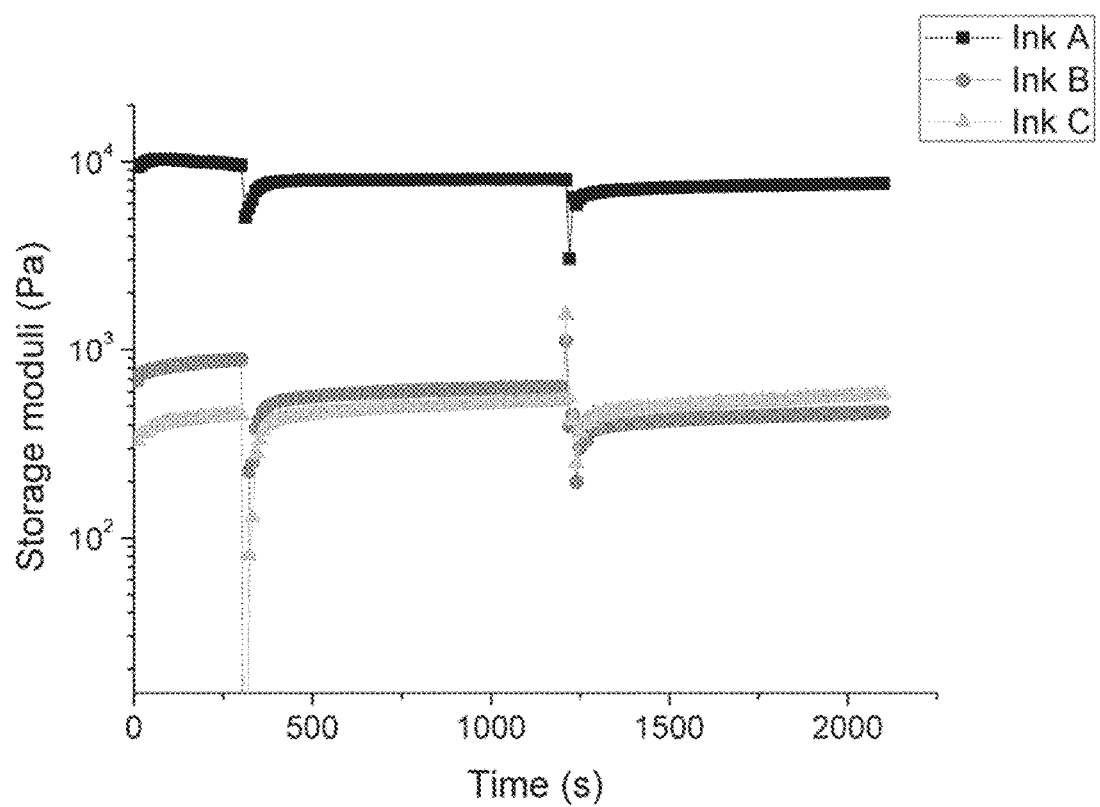
FIG. 4. is a graphical illustration of the shear recovery for the nanocomposite composition of the present technology (Ink A) and comparative ink compositions (Ink B—uncoated silica nanoparticles; Ink C—no nanoparticles).

The rheological properties of Ink A, Ink B, and Ink C were analyzed using a rheometer. Shear-thinning of Ink A was greatly increased compared to Ink C. As provided in FIG. 3, the highest viscosity of Ink A was 5.25-times higher than that of Ink C when measured at a low shear rate, whereas at a high shear rate, the viscosity of Ink A was lower than that of Ink C. Ink B, having the uncoated silica nanoparticles, resulted in only a 2.1-fold increase in viscosity at a low shear rate compared with that of the Ink C. Additionally, the viscosity of Ink B at a high shear rate was nearly the same as that of Ink A. Accordingly, the results demonstrate that Ink A created a greater number of reversible electrostatic interactions with polymers than did Ink B. FIG. 4 illustrates that Ink A recovers its network in <1 min after removal of high shear stress. Ink A also exhibited a 10-fold higher storage modulus after two shear stress cycles compared to Ink C.

Figure 5:
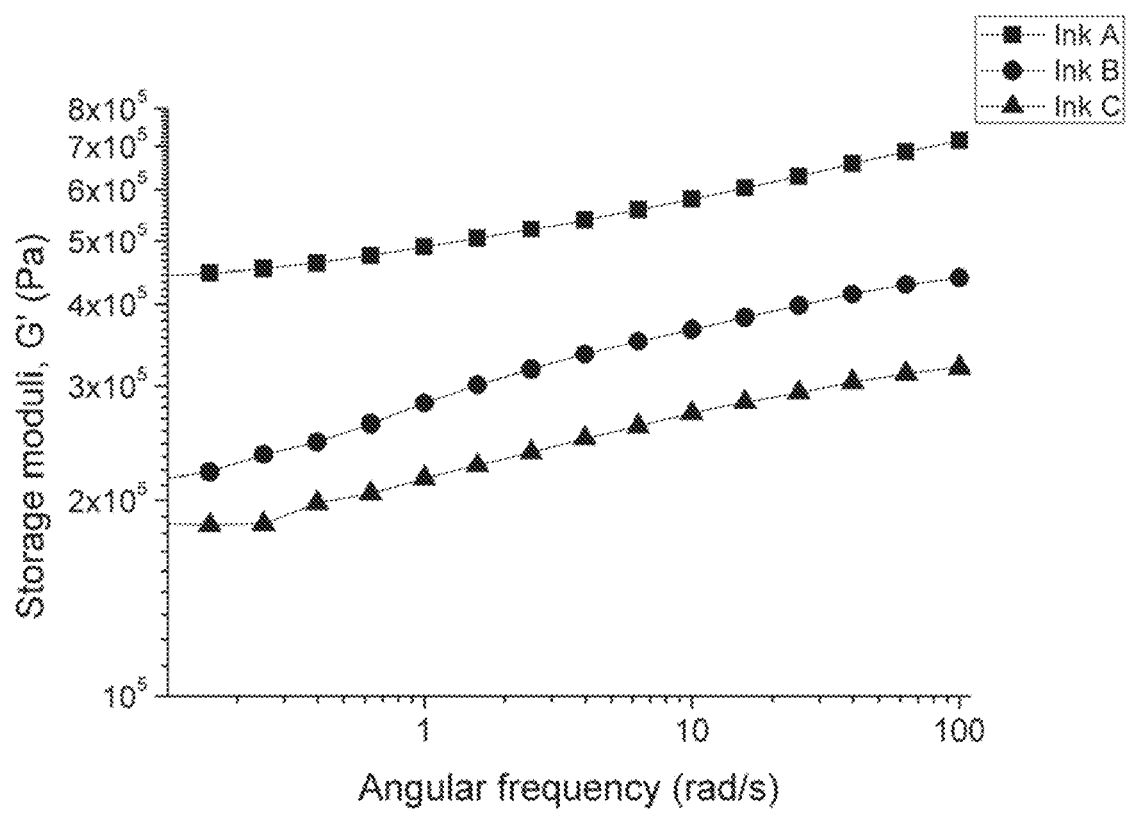
FIG. 5 is a graphical illustration of the storage moduli for the nanocomposite composition of the present technology (Ink A) and comparative ink compositions (Ink B—uncoated silica nanoparticles; Ink C—no nanoparticles).

Ink A and Ink C were subjected to ionic cross-linking by incubating each ink in a 100 mM $CaCl_2$ solution, which resulted in the formation of double cross-linked ink gels. After the ionic cross-linking, both compressive and tensile strength of the ink gels were assessed using a rheometer and a texture analyzer. The storage modulus of Ink A was 2 to 2.5-times higher than Ink C (FIG. 5). Table 1 illustrates that the secant modulus for Ink A was approximately 50% greater than Ink C, while the ultimate stress and ultimate strain were not significantly different.

TABLE 1

Tensile properties of Ink A (P-NP ink gel) and Ink C (no nanoparticles).

| | Secant Modulus [MPa] ± Std. Dev. | Ultimate Stress [MPa] ± Std. Dev. | Ultimate Strain [%] ± Std. Dev. |
|---|---|---|---|
| Ink A | 0.32 ± 0.01 | 0.227 ± 0.020 | 48.19 ± 4.7 |
| Ink C | 0.20 ± 0.01 | 0.212 ± 0.016 | 55.66 ± 4.5 |

The exemplary nanocomposite composition of the present technology (Ink A) demonstrated cross-linking of the gelling agents to provide a hydrogel with improved viscosity and superior shear-thinning properties over the comparative compositions (Ink B and Ink C). Further, the exemplary nanocomposite composition of the present technology showed a unexpectedly high mechanical strength (Table 1) over gelling agents alone, both before and after externally triggered cross-linking.

Example 3: Preparation of Nanocomposite Ink with Cationic Amine-Functionalized Nanoparticles A dispersion of commercially available triethoxylpropylaminosilane functionalized silica nanoparticles ($NH_2$-NP, +33 mV, 33 nm; from Sigma-Aldrich) was used as cationic nanoparticle cores in accordance with the present technology as disclosed herein. Ink D was prepared by combining the $NH_2$-NP dispersion with 3 wt. % alginate and 3 wt. % gellan gum to a final amount of NH-NP of 6 wt. %. Following the same procedure as above, inks were prepared with a dispersion of uncoated Ludox silica nanoparticles (Si-NP, −28 mV, 28 nm) (Ink E) and with no nanoparticles (Ink F). Ink D and Ink E each exhibited increased viscosity that was about 3-times higher than Ink F, and enhanced shear-thinning properties. Ink D exhibited a higher storage modulus of 2,500 Pa than that of Ink E (790 Pa) and Ink F (580 Pa).

Ink D, Ink E, and Ink F were subjected to additional cross-linking by incubating each ink in a 100 mM aqueous solution of $CaCl_2$ for 30 min. Following incubation, Ink D exhibited a 220% increase in its storage modulus (550 kPa), where that of Ink E and Ink F only exhibited a storage modulus of 110 kPa and 170 kPa, respectively. Thus, the exemplary nanocomposite composition of the present technology (Ink D) exhibited improved viscosity, shear-thinning properties, and unexpectedly high mechanical strength compared to comparative compositions (Ink E and Ink F).

Figure 9:
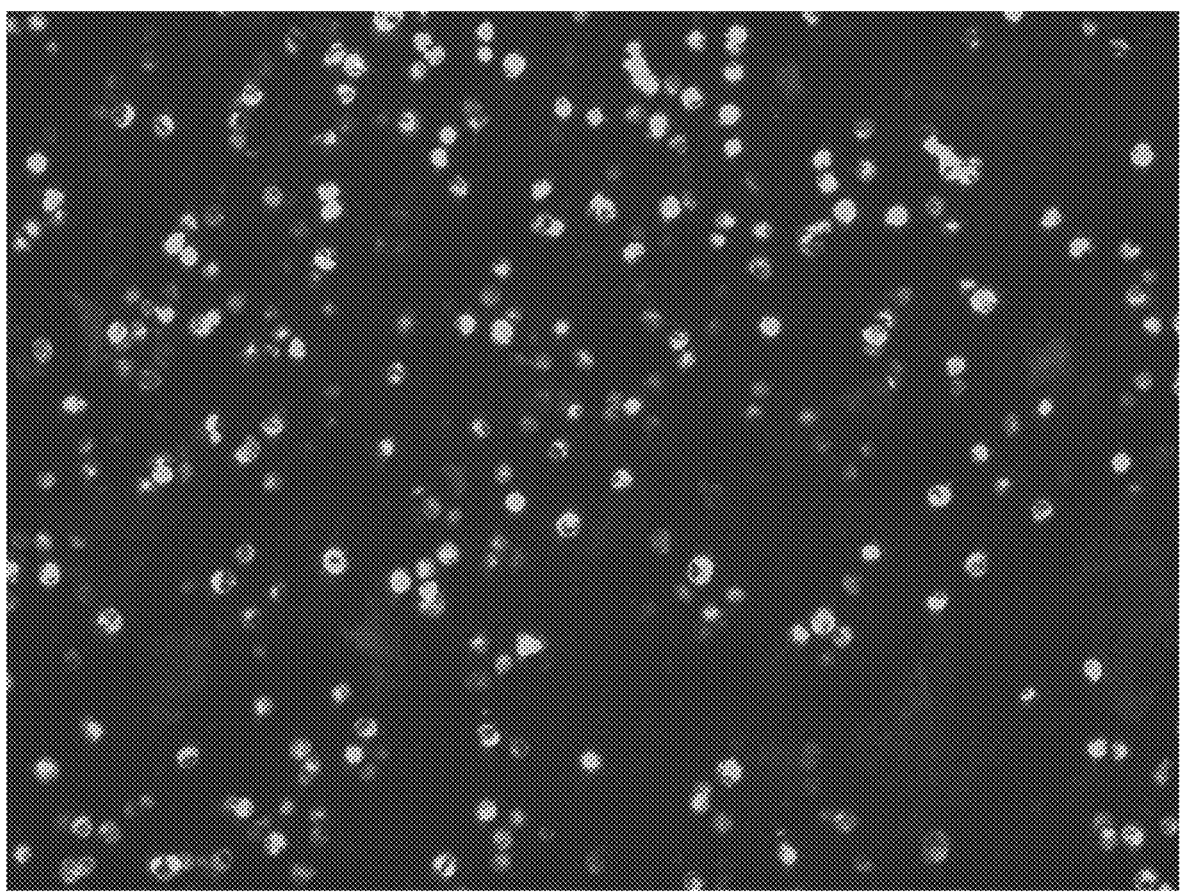
FIG. 9 shows the Live/Dead staining of bovine chondrocytes in Ink G (Example 3) at day 21.

Ink G was prepared following the same preparation as Ink D. In addition, bovine chondrocytes were included in the nanocomposite composition of Ink G and cultured for 3 weeks. The viabilities of cells in Ink G were 94% at day 0 and 95% at day 21 as measured via a Live/Dead assay (FIG. 9).

Example 4: Printing of a Three-Dimensional Structure Using Nanocomposite Ink

Figure 6A:
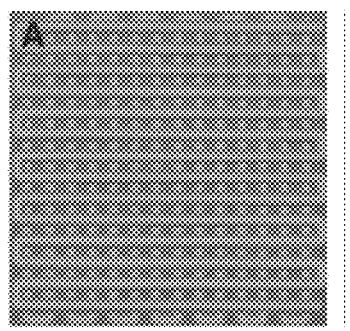
FIGS. 6A-6C show the grid design used for printing (FIG. 6A), the printed Ink C (no nanoparticles) before (left, FIG. 6B) and after 30 min of ionic cross-linking (right, FIG. 6B), and the printed nanocomposite composition of the present technology (Ink A) before (left, FIG. 6C) and after 30 min ionic cross-linking (right, FIG. 6C).
Figure 6B:
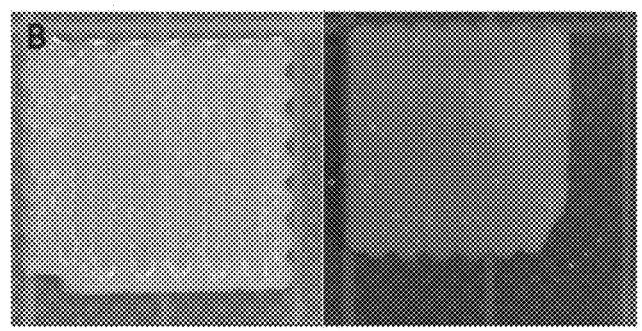
Figure 6C:
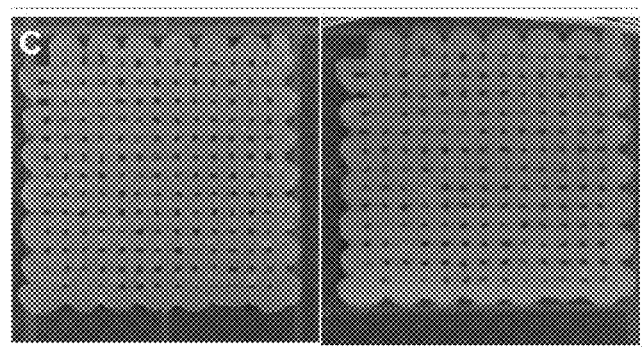
Figure 7A:
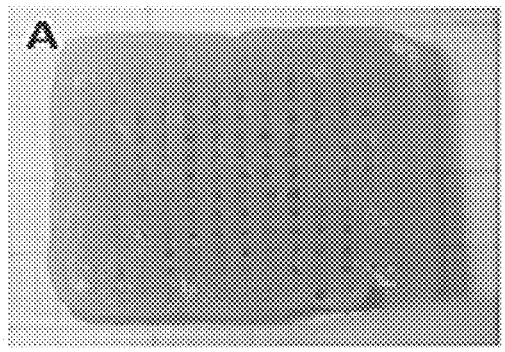
FIGS. 7A-7B show printed structures according to layered grid designs, where
Figure 7A:
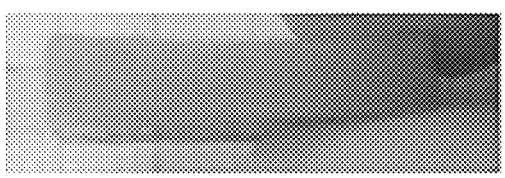
Figure 7B:
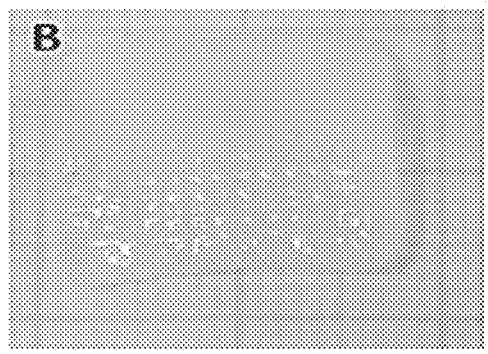
Figure 7B:
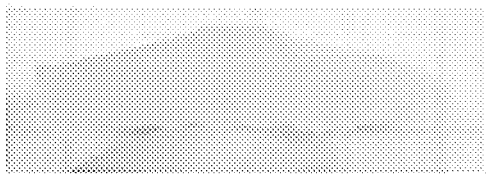
Figure 8A:
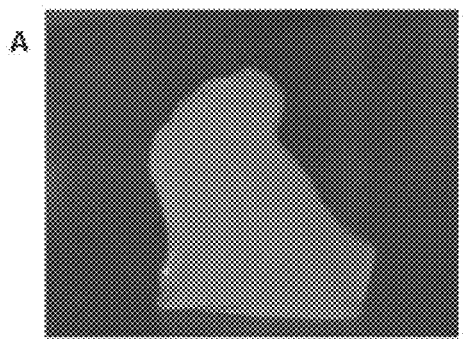
FIGS. 8A-8C shows 3D-printed 1-cm cubes using the nanocomposite composition of the present technology (Ink A) and comparative ink having no nanoparticles (Ink C).
Figure 8B:
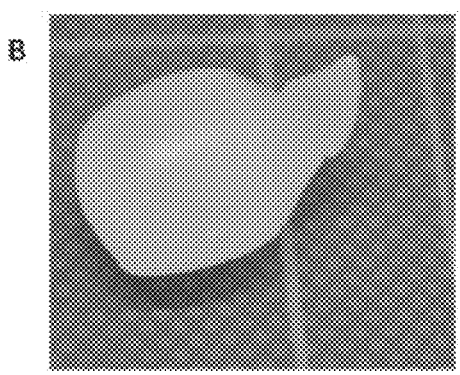
Figure 8C:
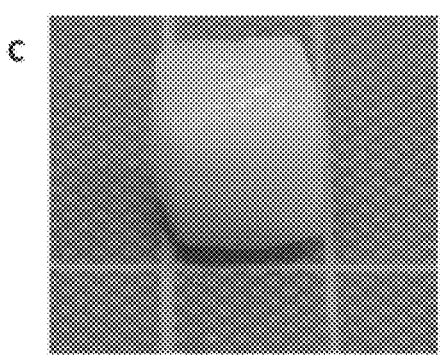

Porous 3D structures were printed using Ink A, Ink C, and Ink D, as disclosed in Examples 2 and 3, according to the grid design (FIG. 6A). The inks were printed using an extrusion-based 3D printer, at an extrusion rate of 20 mm/s (Ink A and Ink D) and 14 mm/s (Ink C). Following 3D printing of each ink, each 3D structure was subjected to $Ca^{2+}$ cross-linking for 30 min. When the structure was printed using Ink C, the resultant 3D structure exhibited shrinkage, where the length of each side was reduced by 15% after 30 min (from 2 cm in the design to 1.7 cm in the printed Ink C gel structure) (FIG. 6B). The 3D structure printed from Ink C exhibited shrinkage during printing and $Ca^{2+}$ incubation, which is attributed to pore collapse and swelling. In contrast, the printed 3D structure using Ink A maintained its dimensions without shrinking, and the pore structure was retained even after $Ca^{2+}$ cross-linking (FIG. 6C). The total pore area of the printed grid (0.256 $cm^2$) and the design (0.233 $cm^2$) differed by only 10% for Ink A. FIGS. 7A-7B illustrate the difference in swelling behaviors between Ink A and Ink C. Larger cube-shaped structures were also printed using Ink A and Ink C. However, the printed 3D structure of Ink C underwent a high degree of swelling, which resulted in greater deviation from the design (FIGS. 8A and 8C). The observed dome-like structure (FIG. 8B) resulted from swelling of the 3D structure of Ink C. In contrast, the Ink A printed 3D structure maintained its shape and dimensions. Another important observation was the difference in printing speed. When Ink C was printed at 20 mm/s, it resulted in printing failure. In contrast, Ink A printed well at 20 mm/s with high structural fidelity (FIG. 8C).

The exemplary nanocomposite composition of the present technology (Ink A) was deposited in accordance methods described herein for extrusion 3D printing of three-dimensional structures derived from computer based models. The resultant three-dimensional structure exhibited superiorly high structural fidelity and a surprisingly low degree of swelling over comparative compositions.

Following the procedure discussed above, Ink D (Example 3) was used to print a three-dimensional structure with an extrusion-based 3D printer. Ink D was printed at an extrusion rate of 20 mm/s to obtain a three-dimensional structure with high structural fidelity. The resultant structure of Ink D exhibited no line-merging between printed layers, and the swelling and shrinkage of edges were greatly suppressed during ionic cross-linking, which were attributed to high mechanical strength of Ink D and cross-linked structure. Ink G was similarly used to print a three-dimensional structure which likewise exhibited high structural fidelity, suppression of swelling and shrinkage during ionic cross-linking, and high mechanical strength.

The above results illustrates the nanocomposite compositions of the present technology allow for high-fidelity 3D structures that maintain their shape when formed, handled, and implanted. Furthermore, the results illustrate the 3D structures can contribute to applications of bioprinted tissues where enhanced mechanical properties are required.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A nanocomposite composition comprising:
  about 0.1 wt. % to about 40 wt. % of nanoparticles by weight of the composition;
  about 0.1 wt. % to about 50 wt. % of one or more gelling agents by weight of the composition; and
  a solvent comprising a protic solvent;
  wherein the nanoparticles have a net cationic charge.

B. The nanocomposite composition of Paragraph A, wherein the nanoparticles comprise (a) cationic nanoparticle cores, or (b) non-cationic nanoparticle cores with a cationic coating material disposed on the outer surface of each non-cationic nanoparticle core, or (c) a mixture of (a) and (b).

C. The nanocomposite composition of Paragraph A or Paragraph B, wherein the nanoparticles have a weight average diameter of about 1 nm to about 300 nm.

D. The nanocomposite composition of any one of Paragraphs A-C, wherein the nanoparticles have a weight average diameter of about 25 nm to about 200 nm.

E. The nanocomposite composition of any one of Paragraphs A-D, wherein the composition comprises about 1 wt. % to about 10 wt. % of the nanoparticles.

F. The nanocomposite composition of any one of Paragraphs A-E, wherein the cationic nanoparticle cores comprise chitosan nanoparticles, amine-functionalized silica nanoparticles, amine-functionalized polystyrene nanoparticles, cationic polyamidoamine dendrimer (PAMAM) nanoparticles, and combinations of any two or more thereof.

G. The nanocomposite composition of any one of Paragraphs A-E, wherein the non-cationic nanoparticle cores are selected from non-ionic nanoparticle cores, anionic nanoparticle cores, or a combination thereof.

H. The nanocomposite composition of Paragraph G, wherein the non-ionic nanoparticle cores comprise polystyrene nanoparticles, poly(D,L-lactide-co-glycolide) nanoparticles, graphene nanoparticles, poly(ethylene glycol) ("PEG")-polylactide nanoparticles, cellulose nanoparticles, magnetic nanoparticles, silver nanoparticles, gold nanoparticles, albumin nanoparticles, silk nanoparticles, gelatin nanoparticles, elastin nanoparticles, or a combination of any two or more thereof.

I. The nanocomposite composition of Paragraph G, wherein the anionic nanoparticle cores comprise silica nanoparticles, mesoporous silica nanoparticles, biodegradable silica nanoparticles, carboxylate-functionalized polystyrene nanoparticles, or a combination of any two or more thereof.

J. The nanocomposite composition of any one of Paragraphs A-E and G-I, wherein the cationic coating material comprises branched poly(ethyleneimine), linear poly(ethyleneimine), poly(allylamine), polylysine, polyarginine, cetyltrimethylammonium bromide (CTAB), guanidine, or a combination of any two or more thereof.

K. The nanocomposite composition of any one of Paragraphs A-J, wherein the one or more gelling agents comprise alginate, alginate sulfate, gellan gum, acylated gellan gum, gellan sulfate, carboxymethylcellulose, carrageen, carrageen sulfate, guar gum, cassia gum, konjac gum, Arabic gum, ghatti gum, locust bean gum, xanthan gum, xanthan gum sulfate, hyaluronic acid, xanthan gum, xanthan gum sulfate, dextran, chondroitin sulfate, heparin, heparin sulfate, gelatin, collagen, polysiloxanes, or a combination of any two or more thereof.

L. The nanocomposite composition of any one of Paragraphs A-K, wherein the one or more gelling agents comprise alginate, alginate sulfate, gellan gum, acylated gellan gum, gellan gum sulfate, or a combination of any two or more thereof.

M. The nanocomposite composition of any one of Paragraphs A-L, wherein the composition comprises about 2 wt. % to about 10 wt. % of the one or more gelling agents.

N. The nanocomposite composition of any one of Paragraphs A-M, wherein the composition comprises
  about 2 wt. % to about 7 wt. % of nanoparticles having a weight average diameter of about 25 nm to about 200 nm and
  about 2 wt. % to about 10 wt. % of the one or more gelling agents.

O. The nanocomposite composition of any one of Paragraphs A-N, wherein a weight ratio of the nanoparticles to the one or more gelling agents is about 1:20 to about 20:1.

P. The nanocomposite composition of any one of Paragraphs A-O, a weight ratio of the nanoparticles to the one or more gelling agents is about 1:1 to about 1:5.

Q. The nanocomposite composition of any one of Paragraphs A-P, wherein the solvent comprises water.

R. The nanocomposite composition of any one of Paragraphs A-Q, wherein the nanocomposite composition further comprises one or more cells, tissue, growth factors, drugs, cytokines, biologics, siRNA, DNA, and antioxidants.

S. The nanocomposite composition of Paragraph R, wherein the cells are autologous or allogeneic cells.

T. The nanocomposite composition of Paragraph R or Paragraph S, wherein the cells comprise primary chondrocytes, primary chondrocytes, chondroprogenitor cells, chondroblasts, mesenchymal stem cells, induced pluripotent stem cells, adipose-derived stem cells, neural crest derived stem cells, fibroblasts, keratinocytes, cardiomyocytes, or a combination of any two or more thereof.

U. A method of preparing a three-dimensional structure, wherein the method comprises
  using a nanocomposite composition of any one of Paragraphs A-T to fabricate a three-dimensional structure.

V. The method of Paragraph U, wherein the method further comprises providing the nanocomposite composition prior to fabricating the three-dimensional structure.

W. The method of Paragraph U or Paragraph V, wherein the method further comprises contacting the three-dimensional structure with a cross-linking agent subsequent to fabricating the three-dimensional structure.

X. The method of any one of Paragraphs U-W, wherein the using fabricates the three-dimensional structure of an organ, preferably a contralateral organ.

Y. The method of any one of Paragraphs U-X, wherein the using comprises ink jet printing, bioprinting, extrusion printing, or layer-by-layer printing.

Z. The method of any one of Paragraphs W-Y, wherein the cross-linking agent comprises a monovalent cation, a divalent cation, a trivalent cation, an enzyme, hydrogen peroxide, horseradish peroxidase, photo initiator, or a combination of any two or more thereof.

AA. The method of any one of Paragraphs U-Z, wherein the method further comprises contacting the three-dimensional structure with cells, tissues, or both.

AB. The method of any one of Paragraphs U-AA, wherein the method further comprises contacting the three-dimensional structure with one or more growth factors.

AC. The method of any one of Paragraphs U-AB, wherein the method further comprises contacting the three-dimensional structure with one or more of drugs, cytokines, biologics, siRNA, DNA, and antioxidants.

AD. A kit for fabricating a nanoparticle composition, the kit comprising nanoparticles having a net cationic charge;
one or more gelling agents; and
instructions for generation of the nanocomposite composition,
wherein the nanocomposite composition comprises
about 0.1 wt. % to about 40 wt. % of the nanoparticles by weight of the composition;
about 0.1 wt. % to about 50 wt. % of the one or more gelling agents by weight of the composition; and
a solvent comprising a protic solvent.

AE. The kit of Paragraph AD, wherein the nanoparticles comprise (a) cationic nanoparticle cores, or (b) non-cationic nanoparticle cores with a cationic coating material disposed on the outer surface of each non-cationic nanoparticle core, or (c) a mixture of (a) and (b).

AF. The kit of Paragraph AD or Paragraph AE, wherein the nanoparticles have a weight average diameter of about 1 nm to about 300 nm.

AG. The kit of any one of Paragraphs AD-AF, wherein the one or more gelling agents comprise alginate, alginate sulfate, gellan gum, acylated gellan gum, gellan sulfate, carboxymethylcellulose, carrageen, carrageen sulfate, guar gum, cassia gum, konjac gum, Arabic gum, ghatti gum, locust bean gum, xanthan gum, xanthan gum sulfate, hyaluronic acid, xanthan gum, xanthan gum sulfate, dextran, chondroitin sulfate, heparin, heparin sulfate, gelatin, collagen, polysiloxanes, or a combination of any two or more thereof.

AH. A three-dimensional structure obtained or obtainable by the method of any one of Paragraphs U-AC.

Other embodiments are set forth in the following claims, along with the full scope of equivalents to which such claims are entitled.

What is claimed is:

1. A nanocomposite hydrogel composition comprising:
   about 1 wt. % to about 10 wt. % of nanoparticles by weight of the composition;
   about 1 wt. % to about 10 wt. % of one or more gelling agents by weight of the composition, wherein the one or more gelling agents comprise alginate, alginate sulfate, gellan gum, acylated gellan gum, gellan sulfate, or a combination of any two or more thereof, wherein a weight ratio of the nanoparticles to the one or more gelling agents is about 1:20 to about 20:1; and
   a solvent comprising a protic solvent;
   wherein the nanoparticles have a net cationic charge, and the nanoparticles interact electrostatically with the one or more gelling agents to form the nanocomposite hydrogel composition.

2. The nanocomposite hydrogel composition of claim 1, wherein the nanoparticles comprise (a) cationic nanoparticle cores, or (b) non-cationic nanoparticle cores with a cationic coating material disposed on the outer surface of each non-cationic nanoparticle core, or (c) a mixture of (a) and (b).

3. The nanocomposite hydrogel composition of claim 2, wherein the cationic nanoparticle cores comprise chitosan nanoparticles, amine-functionalized silica nanoparticles, amine-functionalized polystyrene nanoparticles, cationic polyamidoamine dendrimer (PAMAM) nanoparticles, and combinations of any two or more thereof.

4. The nanocomposite hydrogel composition of claim 2, wherein the non-cationic nanoparticle cores are selected from non-ionic nanoparticle cores, anionic nanoparticle cores, or a combination thereof.

5. The nanocomposite hydrogel composition of claim 4, wherein the non-ionic nanoparticle cores comprise polystyrene nanoparticles, poly(D,L-lactide-co-glycolide) nanoparticles, graphene nanoparticles, poly(ethylene glycol) ("PEG")-polylactide nanoparticles, cellulose nanoparticles, magnetic nanoparticles, silver nanoparticles, gold nanoparticles, albumin nanoparticles, silk nanoparticles, gelatin nanoparticles, elastin nanoparticles, or a combination of any two or more thereof.

6. The nanocomposite hydrogel composition of claim 4, wherein the anionic nanoparticle cores comprise silica nanoparticles, mesoporous silica nanoparticles, biodegradable silica nanoparticles, carboxylate-functionalized polystyrene nanoparticles, or a combination of any two or more thereof.

7. The nanocomposite hydrogel composition of claim 2, wherein the cationic coating material comprises branched poly(ethyleneimine), linear poly(ethyleneimine), poly(allylamine), polylysine, polyarginine, cetyltrimethylammonium bromide (CTAB), guanidine, or a combination of any two or more thereof.

8. The nanocomposite hydrogel composition of claim 1, wherein the nanoparticles have a weight average diameter of about 1 nm to about 300 nm.

9. The nanocomposite hydrogel composition of claim 1, wherein the nanoparticles have a weight average diameter of about 25 nm to about 200 nm.

10. The nanocomposite hydrogel composition of claim 1, wherein the one or more gelling agents further comprise carboxymethylcellulose, carrageen, carrageen sulfate, guar gum, cassia gum, konjac gum, Arabic gum, ghatti gum, locust bean gum, xanthan gum, xanthan gum sulfate, hyaluronic acid, xanthan gum, xanthan gum sulfate, dextran, chondroitin sulfate, heparin, heparin sulfate, gelatin, collagen, polysiloxanes, or a combination of any two or more thereof.

11. The nanocomposite hydrogel composition of claim 1, wherein the composition comprises about 2 wt. % to about 10 wt. % of the one or more gelling agents.

12. The nanocomposite hydrogel composition of claim 1, wherein the composition comprises
   about 2 wt. % to about 7 wt. % of nanoparticles having a weight average diameter of about 25 nm to about 200 nm; and
   about 2 wt. % to about 10 wt. % of the one or more gelling agents.

13. The nanocomposite hydrogel composition of claim 1, wherein the nanocomposite composition further comprises one or more cells, tissue, growth factors, drugs, cytokines, siRNA, DNA, and antioxidants.

14. The nanocomposite hydrogel composition of claim 1, wherein the weight ratio of the nanoparticles to the one or more gelling agents is about 4:1 to about 1:4.

15. A method of preparing a three-dimensional structure, wherein the method comprises
   using the nanocomposite hydrogel composition of claim 1 to fabricate a three-dimensional structure.

16. The method of claim 15, wherein the method further comprises contacting the three-dimensional structure with a cross-linking agent subsequent to fabricating the three-dimensional structure.

17. The method of claim 15, wherein the using fabricates the three-dimensional structure of an organ.

18. A kit for fabricating a nanocomposite hydrogel composition of claim 1, the kit comprising:
nanoparticles having a net cationic charge;
one or more gelling agents; and
instructions for generation of the nanocomposite hydrogel composition,
wherein the nanocomposite hydrogel composition comprises
about 1 wt. % to about 10 wt. % of the nanoparticles by weight of the composition;
about 1 wt. % to about 10 wt. % of the one or more gelling agents by weight of the composition, wherein the one or more gelling agents comprise alginate, alginate sulfate, gellan gum, acylated gellan gum, gellan sulfate, or a combination of any two or more thereof; and
a solvent comprising a protic solvent;
wherein the nanoparticles interact electrostatically with the one or more gelling agents to form the nanocomposite hydrogel composition.

19. The kit of claim 18, wherein the one or more gelling agents further comprise carboxymethylcellulose, carrageen, carrageen sulfate, guar gum, cassia gum, konjac gum, Arabic gum, ghatti gum, locust bean gum, xanthan gum, xanthan gum sulfate, hyaluronic acid, xanthan gum, xanthan gum sulfate, dextran, chondroitin sulfate, heparin, heparin sulfate, gelatin, collagen, polysiloxanes, or a combination of any two or more thereof.

\* \* \* \* \*